United States Patent
Chen et al.

[11] Patent Number: 5,916,595
[45] Date of Patent: Jun. 29, 1999

[54] HMG CO-REDUCTASE INHIBITOR

[75] Inventors: Chih-Ming Chen, Davie; Joseph Chou, Coral Springs; David Wong, Hollywood, all of Fla.

[73] Assignee: Andrx Pharmaceutials, Inc., Fort Lauderdale, Fla.

[21] Appl. No.: 08/989,253

[22] Filed: Dec. 12, 1997

[51] Int. Cl.⁶ ................................................ A61K 9/36
[52] U.S. Cl. ........................................ 424/480; 514/529
[58] Field of Search ............................ 514/529; 424/480

[56] References Cited

U.S. PATENT DOCUMENTS

| | | | |
|---|---|---|---|
| 4,814,183 | 3/1989 | Zentner | 424/485 |
| 4,915,954 | 4/1990 | Ayer et al. | 424/473 |
| 4,946,686 | 8/1990 | McClelland et al. | 424/473 |
| 4,976,967 | 12/1990 | McClelland et al. | 424/473 |
| 5,244,916 | 9/1993 | Bokoch | 514/460 |
| 5,300,288 | 4/1994 | Albright | 424/78.08 |
| 5,350,584 | 9/1994 | McClelland et al. | 424/501 |
| 5,366,738 | 11/1994 | Rork et al. | 424/473 |
| 5,518,730 | 5/1996 | Fuisz | 424/426 |
| 5,543,154 | 8/1996 | Rork et al. | 424/473 |
| 5,582,838 | 12/1996 | Rork et al. | 424/472 |
| 5,616,593 | 4/1997 | Patel et al. | 514/321 |

OTHER PUBLICATIONS

Hatano, Harumi et al., Pharmaceutical Preparation inform of Coated Capsule Releasable at Lower Part of Digestive Tract, Caplus, 1997:195672.

*Primary Examiner*—Jose' G. Dees
*Assistant Examiner*—Michael A. Williamson
*Attorney, Agent, or Firm*—Hedman, Gibson & Costigan, P.C.

[57] ABSTRACT

A controlled release dosage formulation is described which is based on a combination of:
(a) a compressed tablet core which contains an alkyl ester of a hydroxy substituted naphthalene derivative a pharmaceutically acceptable, water swellable polymer and an osmotic agent; and
(b) an outer coating layer which completely covers the osmotic core and comprises a pH sensitive coating agent and a water insoluble polymer.

12 Claims, 3 Drawing Sheets

HMG CO-REDUCTASE INHIBITOR

BACKGROUND OF THE INVENTION

The use of HMG-COA reductase inhibitors for the reduction of serum cholesterol levels is well know. These compounds include alkyl esters of hydroxy substituted naphthalenes which are orally effective in the reduction of serum cholesterol levels. Examples of these compounds include mevastatin which is described in U.S. Pat. No. 3,671,523; lovastatin which is described in U.S. Pat. No. 4,231,938; pravastatin which is described in U.S. Pat. No. 4,346,227; and simvastatin which is described in U.S. Pat. No. 4,444,784. All of these patents are incorporated by reference.

Lovastatin is a metabolite which is produced by the natural fermentation of an fungus of the Aspergillus genus. Lovastatin acts systemically to lower blood serum cholesterol levels by disrupting the biosynthesis of cholesterol in the liver, where 70% to 80% of body cholesterol is produced. Specifically lovastatin interrupts a step in the endogenous production of cholesterol by inhibiting the HMG coenzyme A reductase from combining with bile acids in the digestive tract such that the bile acids are excreted from the body without reabsorption. With synthesis in the liver thusly inhibited, the liver cells must take cholesterol from the bloodstream, and they do so by increasing their production of cell surface receptors for LDL cholesterol. Lovastatin formulations are generally capable of lowering the blood serum cholesterol level by about 30–40%. The other compounds of this class are derived from natural or synthetic sources using well known procedures and have similar mechanisms of activity.

However, it is desirable to enhance the activity of these compounds to achieve even greater reductions of blood serum cholesterol levels in connection with the treatment of hypercholesterolemia and other maladies. Accordingly, the present invention provides a novel controlled release formulation of a compound which is an alkyl ester of a hydroxy substituted naphthalene derivative which provides for a gradual release of the compound. This formulation has been prepared to provide a slow controlled release of these compounds in order to provide a more constant level of bioavailability in order to provide an enhanced effect that cannot be achieved by conventional immediate release dosing. The use of a controlled release form of is believed to be specially useful for those who have meals at irregular times or those who frequently eat snacks between meals. These subjects include night shift workers, airline personnel and travelers, and those individuals with blood sugar problems who eat frequent small meals. In addition, it is believed that the human body synthesizes high amounts of cholesterol during the hours of sleep and it is desirable in certain cases to provide therapeutic level of these compounds during periods of sleep.

Controlled release formulations have been described in U.S. Pat. No. 4,615,698 which have been based on an osmotic dosage form which is designed to collapse and cause the faced surfaces to come into a close contacting arrangement as the drug is delivered through a passageway in the semi-permeable wall of the dosage form. In addition, U.S. Pat. No. 4,503,030 discloses an osmotic dosage form which has a passageway and a semi-permeable membrane consisting of a particular cellulose polymer and a pH sensitive material which could be an enteric coating material. This patent describes the use of 1:1 mixtures of a pH sensitive material and cellulose polymer which are applied at a level of about 7% by weight based on the total weight of the osmotic core tablet and coating material.

The applicants have discovered that a ratio of 0.75:1, and lower, of pH sensitive material to cellulose polymer may be used to provide a stable membrane around an osmotic core tablet at a coating level of 1–4% by weight based on the total weight of the osmotic core tablet and coating material. These osmotic tablets will substantially, completely deliver the compound without the need to provide a passageway in the tablet according to the teachings of the prior art. In addition the osmotic tablet of the invention will provide higher bioavailability and lower peak plasma drug concentrations than are provided by the same weight of the alkyl ester of a hydroxy substituted naphthalene derivative in a conventional immediate release dosage form.

SUMMARY OF THE INVENTION

The present invention provides a controlled release lovastatin dosage formulation which comprises:

(a) a compressed tablet core which contains an alkyl ester of a hydroxy substituted naphthalene derivative, a pharmaceutically acceptable, water swellable polymer and an osmotic agent; and (b) an outer coating layer which completely covers the osmotic core and comprises a pH sensitive coating agent and a water insoluble polymer.

An optional sealing coat may be applied to the compressed tablet core and an optional coating layer comprising an enteric coating agent may be applied under the outer coating layer as an inner coating or as an overcoat over the outer coating layer. The tablet core may be compressed using a smooth faced tablet die. The preferred alkyl ester of a hydroxy substituted naphthalene compound is lovastatin.

Accordingly, it is a primary object of the present invention to provide a controlled release form of an alkyl ester of a hydroxy substituted naphthalene derivative.

It is also an object of the present invention to provide a controlled release dosage formulation of an alkyl ester of a hydroxy substituted naphthalene derivative which substantially completely releases said alkyl ester in about 4 to 30 hours in vitro in a Type 2 USP 23 dissolution apparatus in 2% sodium lauryl sulfate, pH buffer to 7.0 at 37° C. and 50 rpm.

DETAILED DESCRIPTION OF THE INVENTION

Figure 1:
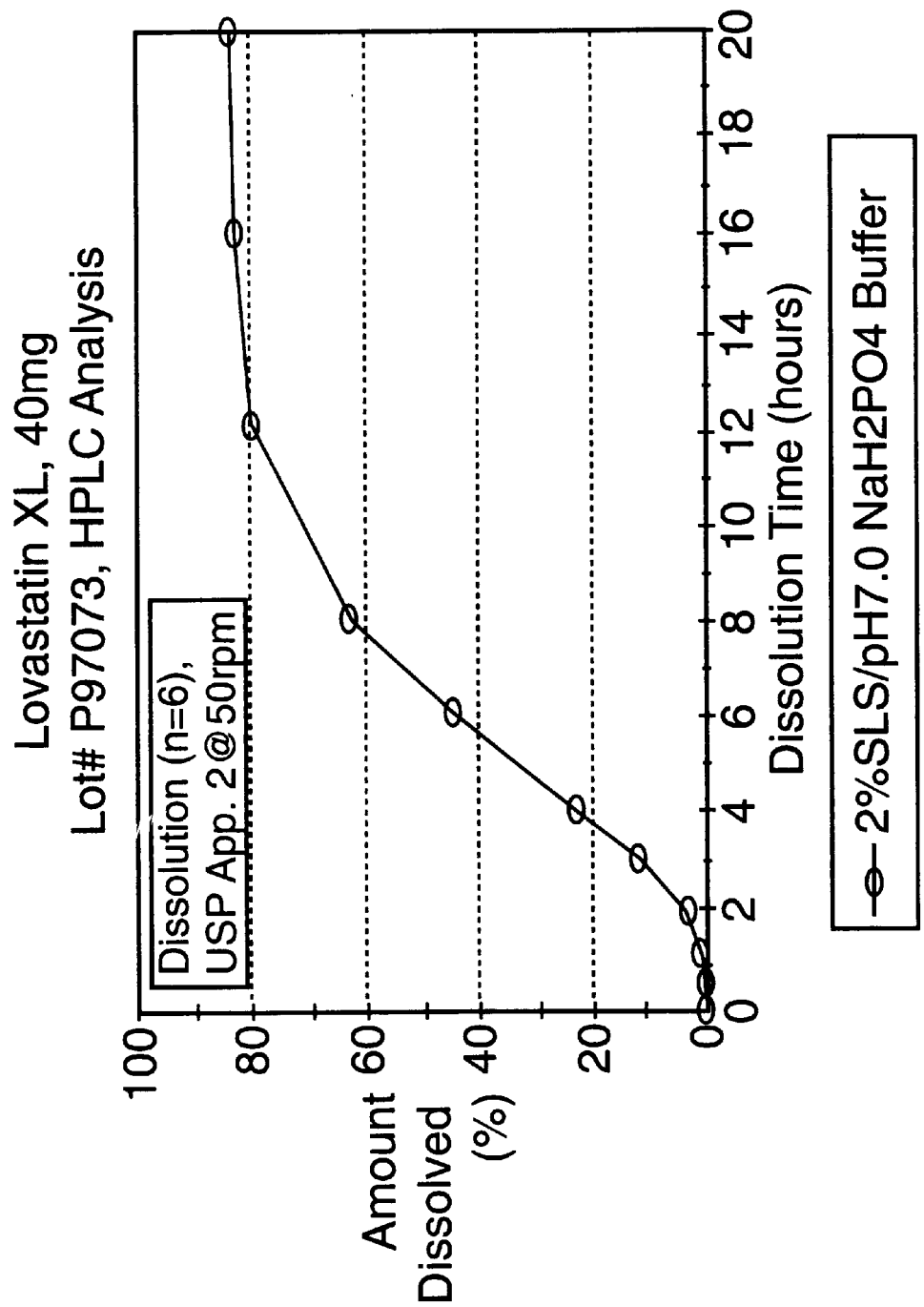
FIG. 1 is a graph of in vitro dissolution data which shows the dissolution profile of the formulation of Example 1 in 2% sodium lauryl sulfate at pH 7.0 in $NaH_2PO_4$ buffer in a USP XXII Type II dissolution apparatus at 50 rpm at 37° C.
Figure 2:
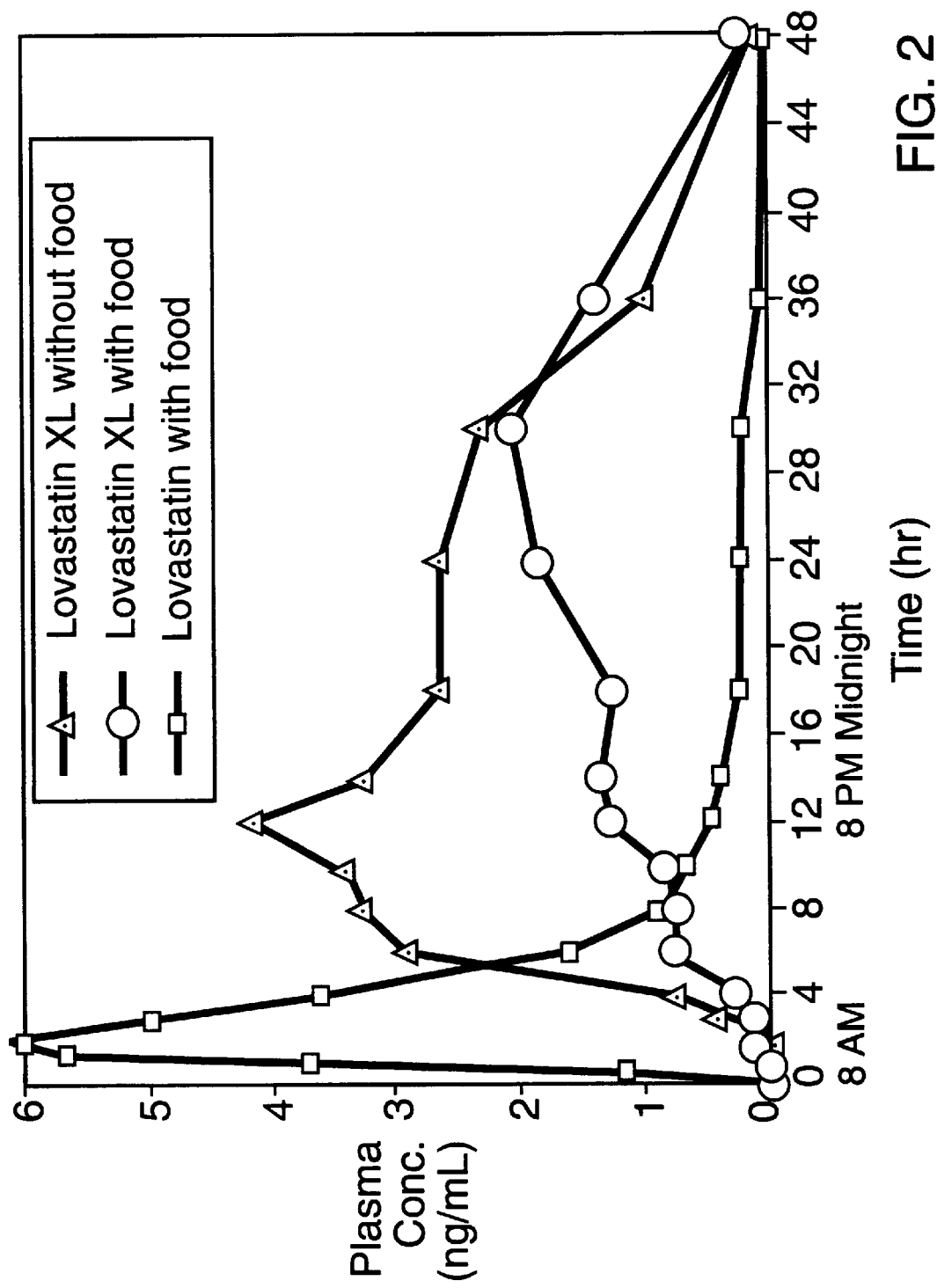
FIG. 2 is a graph of comparative date which shows the in vivo effect of a conventional immediate release dose of 40 mg of lovastatin and the in vivo effect of a extended release dose, according to the invention, of 40 mg of lovastatin.
Figure 3:
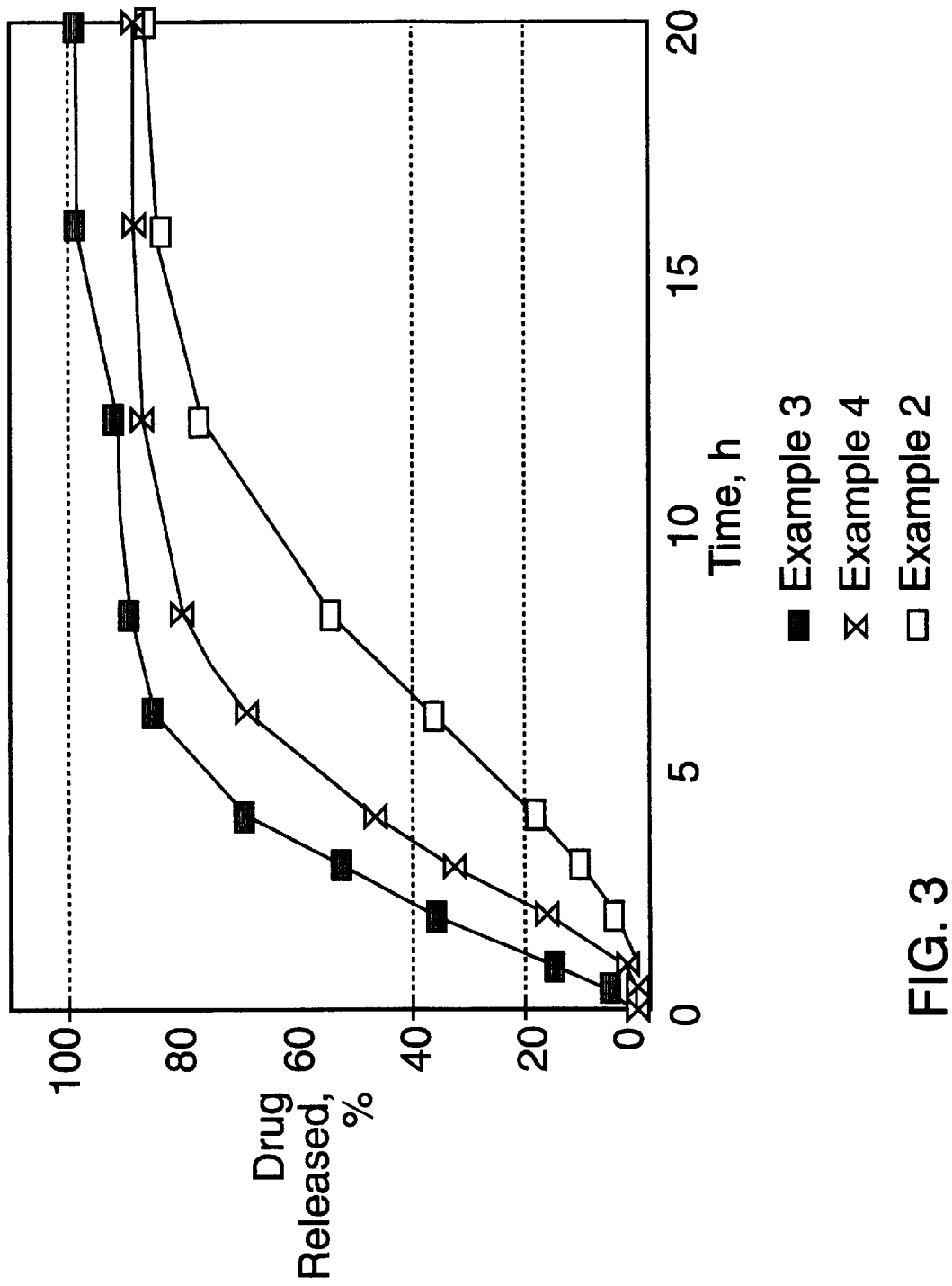
FIG. 3 is a graph of in vitro dissolution data which shows the dissolution profiles of the formulations of Examples 2, 3 and 4 in 2% sodium lauryl sulfate at pH 7.0 in $NaH_2PO_4$ buffer in a USP XXII Type II dissolution apparatus at 50 rpm at 37° C.

The controlled release dosage form is preferably prepared by combining mevastatin, pravastatin, simvastatin or lovastatin with a pharmaceutically acceptable, water swellable polymer and an osmotic agent into a compressed tablet core having an optional first coating for sealing and protection and a second coating comprising a pH sensitive agent water insoluble polymer. Mevastatin, pravastatin, simvastatin and lovastatin are well known compounds that are described in the prior art including the particular patents which have been cited herein. It is also within the scope of the invention to use mixtures of different alkyl esters of hydroxy substituted naphthalenes.

Specifically, a pharmaceutically acceptable, water swellable polymer and an osmotic agent are combined with the drug which may be micronized or unmicronized or amorphous or crystalline and compressed to form the tablet core. The osmotic agent is any non-toxic pharmaceutically acceptable water soluble compound which will dissolve sufficiently in water and increase the osmotic pressure inside the core of the tablet. The osmotic agents include the simple sugars and salts such as sodium chloride, potassium chloride, magnesium sulfate, magnesium sulfate, magnesium chloride, sodium sulfate, lithium sulfate, urea, inositol, sucrose, lactose, glucose, sorbitol, fructose, mannitol, dextrose, magnesium succinate, potassium acid phosphate and the like. The preferred osmotic agent for the tablet core is a simple sugar such as anhydrous lactose in the range of 0–50% by weight, based on the weight of the compressed, uncoated tablet.

The pharmaceutically acceptable, water swellable polymer may be any pharmaceutically acceptable polymer which swells and expands in the presence of water to slowly release the lovastatin. These polymers include polyethylene oxide, methylcellulose, hydroxypropylcellulose, hydroxypropylmethylcellulose and the like. In a preferred embodiment, the water swellable polymer will be polyethylene oxide (obtained from Union Carbide Corporation under the trade name Polyox WSR Coagulant or Polyox WSR N 80). These materials form a viscous gel in water or other solvent system at a sufficient concentration to control the release of the lovastatin. This will generally require a concentration of the pharmaceutically acceptable, water swellable polymer of about 0–50% by weight of the compressed, uncoated tablet.

Binder may be employed in a sufficient amount so that when it is combined with a suitable solvent, mixed with the water soluble osmotic agent and agitated, granules will be formed which may be compressed into a tablet core. Prior to compressing the granules, the conventional solid pharmaceutical diluents such as microcrystalline cellulose, lactose, dextrose and the like may be added to the granule forming mixture in amounts from about 0 to 51% weight based on the weight of the compressed, uncoated tablet. In the present case, the above mentioned osmotic agent, lactose, may function as a binder in the tablet compression step.

In the preparation of the tablets of the invention, various solvents may be used to prepare the granules. In addition, various other diluents, excipients, lubricants, dyes, pigments, dispersants, emulsifiers, etc. may be used to optimize the formulations of the invention.

Additionally, a surfactant is used in the preferred embodiment. The surfactant may be any ionic or non-ionic water soluble surfactant which may be employed in the range of 0–50% by weight or preferably 1–5% by weight. The preferred surfactant for the present formulation is sodium lauryl sulfate but other surfactants such as polysorbate 20, 60 or 80; polyoxl 40 stearate and the like.

Furthermore, the preferred embodiment may comprise a lubricant. Ideally, the lubricant will be in the range of 0.5 to 2.5% by weight of the compressed, uncoated tablet.

After the above described tablet core is formed, it is coated with: 1) an optional protective first coating on the tablet core and/or an optional pH sensitive coating; 2) an outer coating comprising a pH sensitive agent and a water insoluble polymer.

Specifically, a protective first coating may be used at a level in the range of 0–10% by weight which may be applied from a coating system such as Opadry Clear sold by Colorcon Corporation. In an especially preferred embodiment, the Opadry Clear will be 2.83% by weight and will be combined with an osmotic agent in the range of 0–10% by weight. While the osmotic agent may be any salt, low molecular weight molecule or water soluble polymers, the preferred agent is sodium chloride. The osmotic agent is added to the coating system when the coating system is being dispersed into purified water. The coating system which contains the osmotic agent may then be sprayed onto the tablets to form a protective coating layer. As mentioned above, this protective first coating is optional.

An optional inner or over coat over the outer coat may also be applied which comprises a pH sensitive polymer which functions as an enteric polymer in that it does not begin to dissolve until pH conditions in excess of the stomach region are encountered. Generally, the pH sensitive materials do not dissolve and begin to release the active drug until a pH above 3.0 and preferably above 5.5. Materials such as such as Eudragit L (copolymer of poly(methacrylic acid, methylmethacrylate), 1:1 ratio; MW (No. Av. 135,000 - USP Type A) or Eudragit S (copolymer of poly(methacrylic acid, methylmethacrylate, 1:2 ratio MW (No. Av. 135,000 - USP Type B), hydroxypropyl methyl cellulose phthalate, cellulose acetate phthalate, polyvinyl acetate phthalate and the like may be used in the range of 0–3% by weight and preferably,2 to 4 percent by weight of the combined weight of the compressed, uncoated tablet and the inner coating of the pH sensitive polymer.

The outer coating comprises a pH sensitive polymer which functions as an enteric polymer in that it does not begin to dissolve until pH conditions in excess of the pH of the stomach region are encountered and a water insoluble polymer which provide controlled release properties to the coating formulation. The pH sensitive polymer is the same type of material that is described above as the optional inner coating layer. The water insoluble polymer may be a cellulosic polymer such as ethylcellulose, cellulose acylate, cellulose mono-, di- or triacetate. The pH sensitive polymer and the insoluble cellulosic polymer are used at a weight ratio of about 0.1: to 0.75:1 preferably 0.25:1 to 0.5:1 of pH sensitive polymer to water insoluble cellulosic polymer. A combined coating weight of about 0.5–5% by weight and preferably 1 to 4% by weight and especially preferred is 1 to 3% by weight of the gained weight based on the weight of the coated tablet core. Cellulose acetate is the preferred water insoluble polymer and the outer coating is preferably applied as a suspension in acetone.

Furthermore, a plasticizer or combination of plasticizers may be added to the inner, outer or over coating to provide elasticity and shape to the coating. While the plasticizer or combination of plasticizers may be any water soluble or water insoluble formulation in the range of 0–10% by weight and preferably 0.5 to 5% by weight of the outer coating composition. Acetyltributyl citrate is the preferred plasticizer but materials such as acetyl triethyl citrate, dibutyl phthalate, triacetin, diethyl phthalate, polyethylene glycol, propylene glycol and the like may be utilized.

An antioxidant such as BHA or BHT may be added to the tablet core as a stabilizer at a level of 0.001 to 0.01 by weight of the tablet core.

Lastly, a channeling agent is mixed with the aforementioned components of the outer coating. A channelling agent may be employed to increase the porosity of the film coating in order to increase the amount of the fluids that penetrate the tablet core and increase the rate of hydration. This allows the release of the lovastatin after the outer film coat ruptures. Generally, channelling agents may be any salts, surfactants, or short-chain water soluble polymers in a water channel forming effective amount i.e. 1 to 5% by weight, based on the total weight of the core and all coating components. The channeling agents include any pharmaceutically acceptable water soluble salt, surfactant, or short chain water soluble polymer such as sodium chloride, potassium chloride, sucrose, polysorbate-80, hydroxypropyl cellulose, hydroxyethyl cellulose and the like.

Also, the preferred embodiment of the inner or over coating is supplied with an anti-sticking agent such as talc to overcome any tablet to tablet stickiness during the coating process. The amount of anti-sticking agent is an amount which prevents sticking which may be in the range of 0–6% by weight based on the weight of the tablets and the coating materials on a dry weight basis.

Although the applicants do not wish to be bound by any theory by which the invention operates, it is believed that the tablets of the invention release the lovastatin by osmotic pressure. Water is drawn into the tablet and it expands to the point where the outer coating fails in one particular area to form a constricted opening which releases the internal contents of the tablet which contain the drug. Thereafter, the aqueous medium of the tablet shell will continue to release the drug as it dissolves until the osmotic pressure inside the tablet shell equals that of the surrounding environment. At the late stages of the in vivo release of lovastatin, it is believed that the tablet shell will collapse and/or disintegrate completely to substantially completely release the remaining drug. The water insoluble coating is not absorbed in the gastrointestinal tract and is eliminated in the feces.

The tablets of the invention may be made in a smooth faced tablet die. Thereafter the tablet is provided with the outer coating which, because of surface tension, will result in a thinner coating layer over the corners of the tablet which will provide an area in the outer coating which will form a channel to allow intestinal fluid to reach the core of the tablet.

The tablets of the invention will have the following general formula:

| INGREDIENTS | POSSIBLE RANGE, wt % |
|---|---|
| Tablet Core | |
| Alkyl ester of a substituted naphthalene | 3–20 |
| Water Swellable Polymer | 10–40 |
| Antioxidant | 0.001–0.01 |
| Osmotic Agents | 20–80 |
| Surfactant | 0–5 |
| Lubricant | 0–5 |
| Coatings: | |
| Seal Coating | 0–10 |
| Osmotic Agents | 0–10 |
| Inner Coating | |
| Enteric Polymer | 0–30 |
| Anti-sticking Agent | 0–6 |
| Plasticizer | 0–6 |
| Channeling Agents | 0–6 |
| Outer Coating | |
| Blend of Enteric Polymer and Water-insoluble Polymer | 0.5–5 |
| Plasticizer(s) | 0–1 |
| Channeling Agents | 0.2.5 |
| Overcoat | |
| Enteric Polymer | 0–30 |
| Anti-sticking Agent | 0–6 |
| Plasticizer | 0–6 |
| Channeling Agents | 0–6 |
| TOTAL | 100 |

DESCRIPTION OF THE PREFERRED EMBODIMENTS

EXAMPLE 1

A tablet having the following formula was prepared:

| | | |
|---|---|---|
| lovastatin | 11.99 wt % | 40.0 mg |
| Polyox WSR Coagulant, NF* | 4.50 wt % | 15.0 mg |
| Polyox WSR N 80, NF** | 17.98 wt % | 60.0 mg |
| lactose (anhydrous) | 50.65 wt % | 169.0 mg |
| sodium lauryl sulfate | 3.00 wt % | 10.0 mg |
| silicon dioxide Fumed USP/NF | 0.45 wt % | 1.5 mg |
| Myvaplex 600P*** | 1.80 wt % | 6.0 mg |
| Seal Coating: | | |
| Opadry Clear**** | 2.81 wt % | 9.4 mg |
| sodium chloride | 0.93 wt % | 3.1 mg |
| Inner Coating: | | |
| hydroxypropylmethylcell. phthal.55 | 2.27 wt % | 7.58 mg |
| talc | 0.78 wt % | 2.6 mg |
| acetyl tributyl citrate | 0.22 wt % | 0.75 mg |
| sugar, confectioners 6X micronized | 0.62 wt % | 2.08 mg |
| Outer Coating: | | |
| cellulose acetate | 1.00 wt % | 3.32 mg |
| Eudragit S 100[1] | 0.34 wt % | 1.13 mg |
| triacetin | 0.08 wt % | 0.27 mg |
| polyethylene glycol 400 | 0.08 wt % | 0.27 mg |
| sugar, confectioners 6X micronized | 0.50 wt % | 1.66 mg |
| | 100.0 wt % | 333.66 mg |

*polyethylene oxide Mw No av 5,000,000
**polyethylene oxide Mw No av 200,000
***glyceryl monostearate
****mixture containing hydroxypropyl methyl cellulose and polyethylene glycol
[1]Eudragit S 100 (poly(methacrylic acid, methylmethacrylate, 1:2 ratio MW (No. Av. 135,000 - USP Type B)

The following describes the process of making the above described dosage form:
STEP 1, THE TABLET CORE
 (a) Granulation
 1. Pass Polyox WSR N80, sodium lauryl sulfate and anhydrous lactose through a 30 mesh stainless steel screen.
 2. Charge the screened materials and lovastatin (micronized) into a vertical granulator.
 3. Dissolve butylated hydroxy anisole in ethanol.
 4. Mix ethanol, and purified water.
 5. Pre-mix the powder mixture for 5 minutes.
 6. Blend the powder mixture again, add the butylated hydroxyanisole solution and then the ethanol/water mixture.
 7. Dry the granules at 45–50° C. until the moisture content is lower than 1.8 wt %.
 8. Pass the granules through a 1575 mesh using a Comil.

Tabletting
1. Mix Cab-O-Sil and Polyox WSR N80.
2. Pass the mixture of Cab-O-Sil and Polyox WSR N80 through a 24 mesh stainless steel screen with the Polyox WSR Coagulant.
3. Blend the screen materials with lovastatin granules for 15 minutes.
4. Pass Myvaplex through a 30 mesh stainless steel screen and combine with the other screen materials.
5. Blend for five minutes.
6. Compress the blend into tablets (300 mg, round, standard concave, $^{11}/_{32}$") which contain 40 mg of lovastatin.

Seal Coating: Opadry Clear
1. Dissolve sodium chloride in purified water.
2. Disperse Opadry Clear into the sodium chloride solution.
3. Spray lovastatin tablets with the aqueous coating suspension using a coater.

Inner Coating: Hydroxypropyl methylcellulose phthalate 55
1. Dissolve hydroxypropyl methylcellulose phthalate 55 in acetone using a homogenizer.
2. Add acetyl tributyl citrate to the acetone solution and mix it with a homogenizer until a homogenized dispersion is obtained.
3. Add talc and sugar to the solution and mix it with a homogenizer until a homogenized dispersion is obtained.
4. Replace the homogenizer with a magnetic mixer and stir the coating mixture throughout the coating process.
5. Spray the Opadry Clear coated lovastatin tablets with the coating dispersion in a coater.

Outer Coating: cellulose acetate
1. Dissolve cellulose acetate and Eudragit S100 in acetone using a homogenizer.
2. Add polyethylene glycol 400, triactein and sugar to the solution and mix until a homogeneous dispersion is obtained.
3. Spray the coating suspension onto the tablets in a coater.

Release in the above described manner will result in the dissolution profile shown in FIG. 1:

It is believed that administration of the above described micronized Lovastatin in these amounts will be particularly effective in inhibiting the biosynthesis of cholesterol in the liver through interruption of HMG coenzyme A reductase. The dosage of lovastatin should be individualized depending on the desired and/or degree of serum cholesterol that is desired. Generally 10 to 80 mg of lovastatin per day should be administered by mouth depending on the response and the degree of reduction in serum cholesterol level that is indicated.

EXAMPLE 2

A tablet having the following formula was prepared:

| | | |
|---|---|---|
| lovastatin | 12.11 wt % | 40.0 mg |
| Polyox WSR Coagulant, NF* | 4.54 wt % | 15.0 mg |
| Polyox WSR N 80, NF** | 17.71 wt % | 58.5 mg |
| lactose (anhydrous) | 51.13 wt % | 168.9 mg |
| sodium lauryl sulfate | 3.03 wt % | 10.0 mg |
| silicon dioxide Fumed USP/NF | 0.45 wt % | 1.5 mg |
| butylated hydroxy anisole | 0.03 wt % | 0.10 mg |
| Myvaplex 600P*** | 1.82 wt % | 6.0 mg |
| Seal Coating: | | |
| Opadry Clear**** | 2.85 wt % | 9.4 mg |
| sodium chloride | 0.94 wt % | 3.1 mg |
| Inner Coating: | | |
| hydroxypropylmethylcell. phthal.55 | 2.29 wt % | 7.58 mg |
| talc | 0.79 wt % | 2.6 mg |
| acetyl tributyl citrate | 0.23 wt % | 0.75 mg |
| sugar, confectioners 6X micronized | 0.08 wt % | 0.27 mg |
| Outer Coating: | | |
| cellulose acetate | 1.00 wt % | 3.32 mg |
| Eudragit S 100¹ | 0.34 wt % | 1.13 mg |
| triacetin | 0.08 wt % | 0.27 mg |
| polyethylene glycol 400 | 0.08 wt % | 0.27 mg |
| sugar, confectioners 6X micronized | 0.50 wt % | 1.66 mg |
| | 100.0 wt % | 330.35 mg |

*polyethylene oxide Mw No av 5,000,000
**polyethylene oxide Mw No av 200,000
***glyceryl monostearate
****mixture containing hydroxypropyl methyl cellulose and polyethylene glycol
¹Eudragit S 100 (poly(methacrylic acid, methylmethacrylate, 1:2 ratio MW (No. Av. 135,000 - USP Type B)

Coated tablets were prepared using the general procedure of Example 1.

EXAMPLE 3

A tablet having the following formula was prepared:

| | | |
|---|---|---|
| lovastatin | 12.14 wt % | 20.0 mg |
| Polyox WSR Coagulant, NF* | 4.55 wt % | 7.5 mg |
| Polyox WSR N 80, NF** | 17.76 wt % | 29.25 mg |
| lactose (anhydrous) | 51.30 wt % | 84.5 mg |
| sodium lauryl sulfate | 3.04 wt % | 5.0 mg |
| silicon dioxide Fumed USP/NF | 0.46 wt % | 0.75 mg |
| butylated hydroxy anisole | 0.03 wt % | 0.05 mg |
| Myvaplex 600P*** | 1.82 wt % | 3.0 mg |
| Seal Coating: | | |
| Opadry Clear**** | 3.42 wt % | 5.63 mg |
| sodium chloride | 1.14 wt % | 1.88 mg |
| Outer Coating: | | |
| cellulose acetate | 1.43 wt % | 2.36 mg |
| Eudragit S 100¹ | 0.49 wt % | 0.80 mg |
| triacetin | 0.11 wt % | 0.19 mg |
| polyethylene glycol 400 | 0.11 wt % | 0.19 mg |
| sugar, confectioners 6x micronized | 0.72 wt % | 1.18 mg |
| Overcoat: | | |
| hydroxypropylmethylcell. phthal.55 | 0.77 wt % | 1.27 mg |
| talc | 0.30 wt % | 0.49 mg |
| triacetin | 0.12 wt % | 0.20 mg |
| sugar, confectioners 6x micronized | 0.30 wt % | 0.49 mg |
| | 100.0 wt % | 146.73 mg |

*polyethylene oxide Mw No av 5,000,000
**polyethylene oxide Mw No av 200,000
***glyceryl monostearate
****mixture containing hydroxypropyl methyl cellulose and polyethylene glycol
¹Eudragit S 100 (poly(methacrylic acid, methylmethacrylate, 1:2 ratio MW (No. Av. 135,000 - USP Type B)

The following describes the process of making the above described dosage form:

STEP 1, THE TABLET CORE
(a) Granulation
1. Pass Polyox WSR NBO, sodium lauryl sulfate and anhydrous lactose through a 30 mesh stainless steel screen.
2. Charge the screened materials and lovastatin (micronized) into a vertical granulator.

3. Dissolve butylated hydroxy anisole in ethanol.

4. Mix ethanol and purified water.

5. Pre-mix the powder mixture for 5 minutes.

6. Blend the powder mixture again, add the butylated hydroxyanisole solution and then the ethanol/water mixture.

7. Dry the granules at 45–50° C. until the moisture content is lower than 1.8 wt %.

8. Pass the granules through a 1575 mesh using a Comil.

Tabletting

1. Mix Cab-O-Sil and Polyox WSR N80.

2. Pass the mixture of Cab-O-Sil and Polyox WSR N80 through a 24 mesh stainless steel screen with the Polyox WSR Coagulant.

3. Blend the screen materials with lovastatin granules for 15 minutes.

4. Pass Myvaplex through a 30 mesh stainless steel screen and combine with the other screen materials.

5. Blend for five minutes.

6. Compress the blend into tablets (164.72 mg, round, standard concave, 17/64" dia.) which contain 20 mg of lovastatin.

Seal Coating: Opadry Clear

1. Dissolve sodium chloride in purified water.

2. Disperse Opadry Clear into the sodium chloride solution.

3. Spray lovastatin tablets with the aqueous coating suspension using a coater.

Inner Coating: None

Outer Coating: cellulose acetate

1. Dissolve cellulose acetate and Eudragit S100 in acetone using a homogenizer.

2. Add polyethylene glycol 400, triactein and sugar to the solution and mix until a homogeneous dispersion is obtained.

3. Spray the coating suspension onto the tablets in a coater.

Overcoating: Hydroxypropyl methylcellulose phthalate 55

1. Dissolve hydroxypropyl methylcellulose phthalate 55 in acetone using a homogenizer.

2. Add acetyl tributyl citrate to the acetone solution and mix it with a homogenizer until a homogenized dispersion is obtained.

3. Add talc and sugar to the solution and mix it with a homogenizer until a homogenized dispersion is obtained.

4. Replace the homogenizer with a magnetic mixer and stir the coating mixture throughout the coating process.

5. Spray the Opadry Clear coated lovastatin tablets with the coating dispersion in a coater.

EXAMPLE 4

A tablet having the following formula was prepared:

| lovastatin | 12.20 wt % | 20.0 mg |
|---|---|---|
| Polyox WSR Coagulant, NF* | 4.57 wt % | 7.5 mg |
| Polyox WSR N 80, NF** | 17.84 wt % | 29.25 mg |
| lactose (anhydrous) | 51.53 wt % | 84.5 mg |
| sodium lauryl sulfate | 3.05 wt % | 5.0 mg |
| silicon dioxide Fumed USP/NF | 0.46% | 0.75 mg |
| butylated hydroxy anisole | 0.03 wt % | 0.05 mg |
| Myvaplex 600P*** | 1.83 wt % | 3.0 mg |

| Seal Coating: | | |
|---|---|---|
| Opadry Clear**** | 3.43 wt % | 5.63 mg |
| sodium chloride | 1.15 wt % | 1.88 mg |
| Inner Coating: | | |
| None | | |
| Outer Coating: | | |
| cellulose acetate | 1.96 wt % | 3.21 mg |
| Eudragit S 100[1] | 0.66 wt % | 1.09 mg |
| acetyl tributyl citrate | 0.32 wt % | 0.52 mg |
| sugar, confectioners 6× micronized | 0.98 wt % | 1.61 mg |
| | 100.00 wt % | 163.99 mg |

*polyethylene oxide Mw No av 5,000,000
**polyethylene oxide Mw No av 200,000
***glyceryl monostearate
****mixture containing hydroxypropyl methyl cellulose and polyethylene glycol Coated tablets were prepared using the general procedure of Example 3 except that no inner coating was applied and an outer enteric coating was applied as an overcoat over the outer layer.

A comparison of Examples 2, 3 and 4 shows that the following was the weight of the coatings that were applied:

| Example 2 | Inner Coating | 4 wt % |
|---|---|---|
| | Outer Coating | 2 wt % |
| | Over Coating | 0% |
| Example 3 | Inner Coating | 0% |
| | Outer Coating | 3 wt % |
| | Over Coating | 2.5% |
| Example 4 | Inner Coating | 0 wt % |
| | Outer Coating | 4 wt % |
| | Over Coating | 0 wt % |

It is believed that administration of the above described micronized Lovastatin in these amounts will be particularly effective in inhibiting the biosynthesis of cholesterol in the liver through interruption of HMG coenzyme A reductase. The dosage of lovastatin should be individualized depending on the desired and/or degree of serum cholesterol that is desired. Generally 10 to 80 mg of lovastatin per day should be administered by mouth depending on the response and the degree of reduction in serum cholesterol level that is indicated.

The foregoing description of a preferred embodiment of the invention has been presented for purposes of illustration and description. It is not intended to be exhaustive or to limit the invention precise form disclosed. Obvious modifications or variations are possible in light of the above teachings. All such obvious modifications and variations are intended to be within the scope of the appended claims.

We claim:

1. A controlled release formulation containing an alkyl ester of a hydroxy substituted naphthalene compound, said formulation comprising:

(a) a compressed tablet core which contains an alkyl ester of a hydroxy substituted naphthalene compound, a pharmaceutically acceptable, water swellable polymer and an osmotic agent; and (b) an outer coating layer which completely covers the osmotic core and comprises a pH sensitive coating agent, a channeling agent and a water insoluble cellulosic polymer used at a weight ratio of 0.1:1 to 0.75:1 and at a combined coating weight of 0.5–5% by weight.

2. A controlled release formulation as defined in claim 1 wherein the alkyl ester of a hydroxy substituted naphthalene compound is selected from the group consisting of mevastatin, pravastatin, simvastatin and lovastatin.

3. A controlled release dosage form as defined in claim 2 wherein said compressed tablet core is provided with a first coating to seal the tablet core.

4. A controlled release dosage form as defined in claim 2 wherein said compressed tablet core is provided with an inner enteric coating.

5. A controlled release dosage form as defined in claim 2 wherein said compressed tablet core is provided with an overcoat which is an enteric coating.

6. A controlled release dosage form as defined in claim 2 wherein the pharmaceutically acceptable water swellable polymer is polyethylene oxide.

7. A controlled release dosage form as defined in claim 2 wherein the osmotic agent is anhydrous lactose.

8. A controlled release dosage form as defined in claim 2 wherein the pH sensitive coating agent is a copolymer of poly(methacrylic acid and methylmethacrylate.

9. A controlled release dosage form as defined in claim 2 wherein the tablet core contains a surface active agent.

10. A controlled release dosage form as defined in claim 2 wherein the tablet core contains sodium lauryl sulfate.

11. A controlled release dosage form which comprises:
    (a) a compressed tablet core which comprises lovastatin, a polyoxyethylene water swellable polymer and anhydrous lactose;
    (b) an outer coating layer which comprises a mixture of a copolymer of poly(methacrylic acid/methylmethacrylate and a cellulose acetate polymer at a weight ratio of 0.1:1 to 0.75:1.

12. A controlled release dosage formulation which comprises:
    (a) a compressed tablet core comprising lovastatin, a pharmaceutically acceptable, water swellable polymer and an osmotic agent;
    (b) an inner coating layer which comprises a pH sensitive coating agent; and
    (c) an outer coating layer which comprises a pH sensitive coating agent, a channeling agent and a water insoluble cellulosic polymer.

* * * * *